Sept. 17, 1935. O. R. FITZHARDINGE Plant Pat. 140
ROSE
Filed May 6, 1935
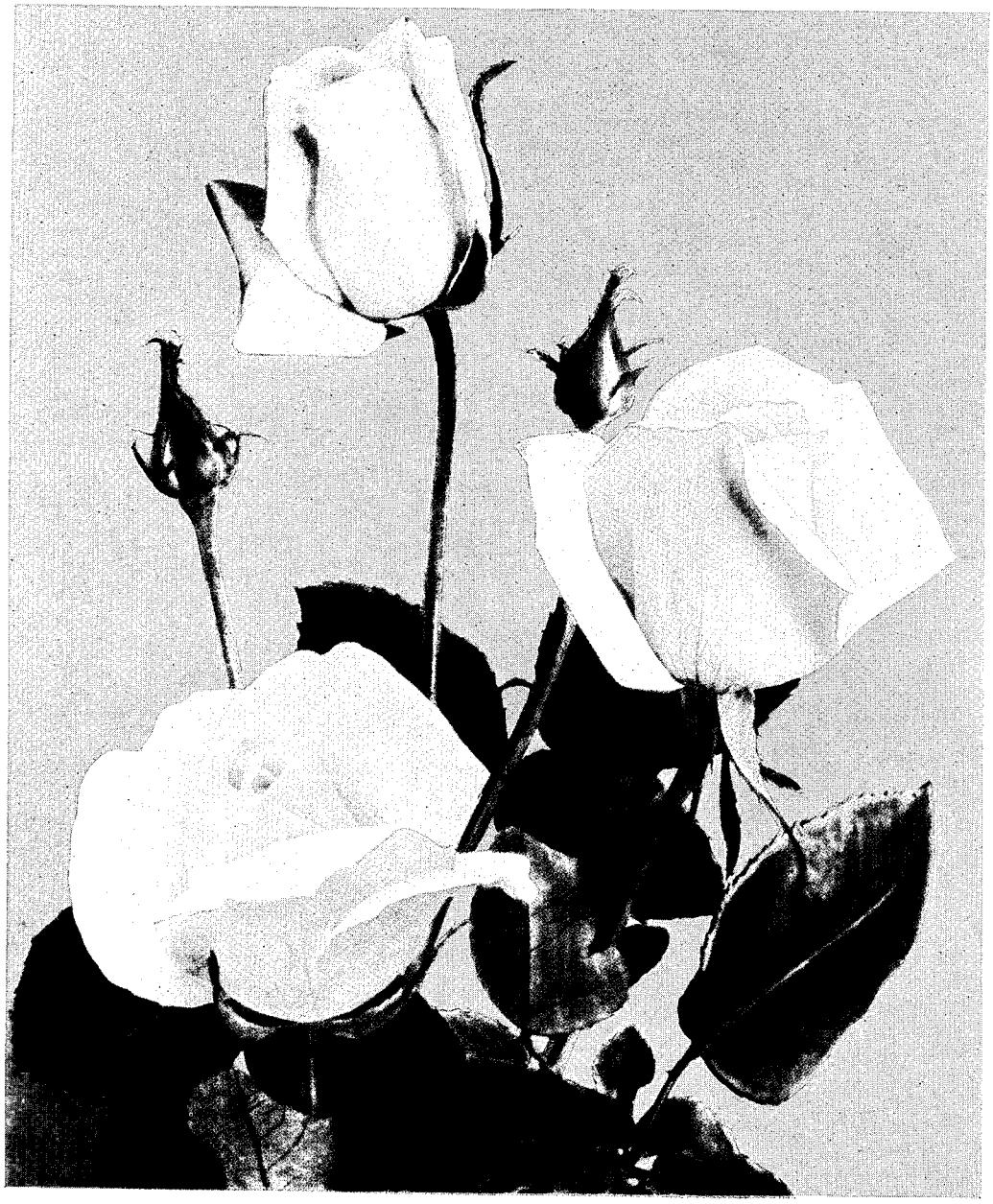
Inventor
Oliver R. Fitzhardinge
By Robbins & Robbins
Attorneys Patented Sept. 17, 1935

UNITED STATES PATENT OFFICE

140

ROSE

Olive R. Fitzhardinge, Warrawee, New South Wales, Australia, assignor to The Conard-Pyle Company, West Grove, Pa.

Application May 6, 1935, Serial No. 20,072

1 Claim. (Cl. 47—61)

The present invention or discovery relates to a new and distinct variety of rose plant, the result of definite breeding efforts to produce a better pink rose than any now in commerce.

To this end I selected for the parents and crossed the hybrid tea roses "Padre" and "Rev. F. Page-Roberts", the latter being used as the female or seed parent and the former as the male or pollen parent.

The resulting new variety is a great improvement on both of its parents, the plant being a stronger and healthier plant than either of its parents and producing more flowers in number than that of both parents together.

In comparison with the known light pink roses, the flower of this new variety is larger, more fragrant and longer lasting and these characteristics in connection with its continuous blooming habit on an exceptionally vigorous and healthy plant, form an unprecedented combination.

Perhaps the nearest rose to this variety for comparison purposes as to the flower is "Mme. Butterfly". However, the bud of the new variety is much larger and longer and the open flower is at least an inch greater in diameter than that of "Mme. Butterfly".

With regard to the plant, that of the new variety is more than twice as large as Mme. Butterfly and produces many more flowers.

This new variety has been asexually reproduced and the characteristics herein referred to have been found to be permanently fixed.

The following is a detailed description of this rose plant and its flower:—

Parentage:—
*Seed parent.*—Rev. F. Page-Roberts.
*Pollen parent.*—Padre.

Classification:—
Hybrid tea.

*Flower*

Blooming habit:—
Continuous.

Bud:—
*Size.*—Extra large.
*Form.*—Ovoid, pointed.
*Color.*—Cameo pink (Ridgeway's chart).
*Sepals.*—Branched, with foliate ends, fold back.
*Calyx.*—Very small, like a slight enlargement of the stem. Smooth. Has same scent as the foliage when rubbed.
*Peduncle.*—Long, smooth, strong, color bronzy green.
*Opening.*—Opens well. Not affected by weather conditions.

Bloom:—
*Size.*—Large. 4½ to 5½ inches.
*Borne.*—Usually singly; rarely in clusters.
*Stems.*—Long, strong.
*Form.*—High centre at first, finally opening slightly cupped but nearly flat, with a few petaloids curled over the stamens.
*Permanence.*—Long lasting.
*Petalage.*—About 25 petals and a few petaloids.
*Color.*—Cameo pink on outside of petals, pale flesh inside.
*Texture.*—Medium heavy.
*Appearance.*—Satiny, both inside and out.
*Form.*—As wide as they are long but not perfectly round.
*Arrangement.*—Moderately loose.
*Persistence.*—Drop off cleanly.

Fragrance:—
*Nature.*—Clove pink.
*Lasting quality.*—Lasts until petals fall.

Genital organs:—
*Stamens, anthers.*—Numerous, buff.
*Stamens, filaments (threads).*—Pink.

Color:—
*Pollen.*—Yellow.
*Styles.*—Loose, uneven length, slender, extend slightly above the stamens.
*Stigmas.*—Flesh colored.
*Ovaries.*—Most all are above the calyx rim; calyx is very shallow.

Fruit:—
*Form.*—Globular.
*Aspect.*—Seeds protrude above calyx rim.
*Sepals.*—Fold back tight against fruit.

*Plant*

Growth:—
Vigorous, upright, branching.

Foliage:—
*Size.*—Large.
*Quantity.*—Better than average.
*Color.*—New foliage, upper side maroon at edges, dark green along midrib; under side vinaceous purple. Mature foliage, upper side dark green; underside green.
*Shape.*—Oval, slightly pointed.
*Texture.*—Leathery, upper side smooth; underside rough. Ribs and veins uniform.
*Edge.*—Serrated.
*Serration.*—Shallow cut, teeth very even.
*Leaf stem.*—New, reddish; mature, green. Prickles on under side.

*Stipules.*—Medium size with pointed tips.
*Disease resistance.*—Unusually resistant.
Wood:—
*New wood.*—Reddish brown.
*Old wood.*—Normal green.
Thorns:—
*Quantity.*—Quite numerous, but probably not more than average H. T.
*Form.*—Wide base; slender half of length; points are lower than centre of base.
*Color when young.*—Maroon.
*Position.*—Irregular.

I claim:—

A new and distinct variety of rose plant characterized by its larger, more fragrant and better lasting flower than now exists among light pink roses, in combination with the characteristic continuous production thereof on an exceptionally vigorous and healthy plant, as shown and described.

OLIVE R. FITZHARDINGE.